(12) United States Patent
Agarwal et al.

(10) Patent No.: US 6,241,768 B1
(45) Date of Patent: *Jun. 5, 2001

(54) PROSTHETIC DEVICE FOR THE REPAIR OF A HERNIA

(75) Inventors: Vishvaroop Agarwal, Piscataway; Carlos Bustamante, Garfield; Gene W. Kammerer, East Brunswick; Donald G. Hill, Hopatcong, all of NJ (US)

(73) Assignee: Ethicon, Inc., Somerville, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/136,036

(22) Filed: Aug. 19, 1998

Related U.S. Application Data

(60) Provisional application No. 60/057,093, filed on Aug. 27, 1997.

(51) Int. Cl.[7] ................ A61F 2/02; A61B 17/08
(52) U.S. Cl. ............. 623/11.11; 606/151; 606/213; 606/215
(58) Field of Search ................. 623/11, 11.11; 128/112.1; 606/151, 215, 213

(56) References Cited

U.S. PATENT DOCUMENTS

| | | |
|---|---|---|
| 636,952 | 11/1899 | Chaney . |
| 2,683,136 | 7/1954 | Higgins ........................ 260/78.3 |
| 2,761,444 | 9/1956 | Luck ............................. 128/92 |

(List continued on next page.)

FOREIGN PATENT DOCUMENTS

| | | | |
|---|---|---|---|
| 0 544 485 B1 | 11/1992 | (EP) | ............ A61B/17/00 |
| 0 544 485 A1 | 6/1993 | (EP) | ............ A61B/17/00 |
| 0 614 650 A2 | 2/1994 | (EP) | ............ A61F/2/00 |
| 0 677 297 A1 | 10/1995 | (EP) | ............ A61L/27/00 |
| 0 692 225 A2 | 1/1996 | (EP) | ............ A61F/2/00 |
| 0 698 395 A1 | 2/1996 | (EP) | ............ A61L/27/00 |
| 0 719 527 A1 | 7/1996 | (EP) | ............ A61F/2/00 |
| 0 744 162 A2 | 11/1996 | (EP) | ............ A61D/2/00 |
| 0 537 955 B1 | 12/1996 | (EP) | ............ A61B/17/12 |
| 0 797 962 A2 | 10/1997 | (EP) | ............ A61F/2/00 |
| WO 90/14796 | 12/1990 | (WO) | ............ A61B/17/12 |
| WO 92/06639 | 4/1992 | (WO) | ............ A61B/17/00 |
| WO 92/13500 | 8/1992 | (WO) | ............ A61F/2/02 |
| WO 92/19162 | 11/1992 | (WO) | ............ A31B/17/04 |
| WO 93/03685 | 3/1993 | (WO) | ............ A61F/2/00 |
| WO 93/13712 | 7/1993 | (WO) | ............ A61B/17/00 |
| WO 93/17635 | 9/1993 | (WO) | ............ A61F/2/00 |
| WO 94/17747 | 8/1994 | (WO) | ............ A61B/19/00 |
| WO 94/27535 | 12/1994 | (WO) | ............ A61F/13/00 |
| WO 95/07666 | 3/1995 | (WO) | ............ A61F/2/02 |
| WO 95/13762 | 5/1995 | (WO) | ............ A61F/2/02 |
| WO 95/31140 | 11/1995 | (WO) | ............ A61B/17/00 |
| WO 95/32687 | 12/1995 | (WO) | ............ A61F/2/00 |
| WO 96/03091 A1 | 2/1996 | (WO) | ............ A61F/2/00 |
| WO 96/03165 A1 | 2/1996 | (WO) | ............ A61L/31/00 |
| WO 96/09795 | 4/1996 | (WO) | ............ A61B/17/00 |
| WO 96/14805 | 5/1996 | (WO) | ............ A61F/2/00 |
| WO 96/41588 | 12/1996 | (WO) | ............ A61F/2/00 |
| WO 97/02789 | 1/1997 | (WO) | ............ A61F/2/00 |
| WO 97/22310 | 6/1997 | (WO) . | |

*Primary Examiner*—David H. Willse
*Assistant Examiner*—Alvin Stewart

(57) ABSTRACT

A prosthesis device for repairing a hernia having an insertion canal made of sheet material for extending through the hernia. The insertion canal is attached at one end to a collar and at the other end to a base that is to be on the inside of the abdominal cavity. The base may be a sheet or a pouch that is to be brought to bear on the inside the wall of the abdominal cavity. The insertion canal providing a simple way of deploying the sheet or pouch against the wall of a abdominal cavity.

8 Claims, 8 Drawing Sheets

U.S. PATENT DOCUMENTS

| | | | | |
|---|---|---|---|---|
| 3,054,406 | | 9/1962 | Usher | 128/334 |
| 3,124,136 | | 3/1964 | Usher | 128/334 |
| 3,707,150 | | 12/1972 | Montgomery et al. | 128/334 R |
| 3,874,388 | | 4/1975 | King et al. | 128/334 R |
| 4,007,743 | | 2/1977 | Blake | 128/334 R |
| 4,013,569 | | 3/1977 | Chiu et al. | 252/8.55 D |
| 4,347,847 | | 9/1982 | Usher | 128/334 |
| 4,548,202 | | 10/1985 | Duncan | 128/334 |
| 4,633,873 | | 1/1987 | Dumican et al. | 128/334 |
| 4,769,038 | | 9/1988 | Bendavid et al. | 623/13 |
| 4,854,316 | | 8/1989 | Davis | 128/334 R |
| 4,917,089 | | 4/1990 | Sideris | 606/215 |
| 5,002,551 | | 3/1991 | Linsky et al. | 606/151 |
| 5,021,059 | | 6/1991 | Kensey et al. | 606/213 |
| 5,092,884 | | 3/1992 | Devereux et al. | 623/11 |
| 5,108,420 | * | 4/1992 | Marks | 606/213 |
| 5,108,421 | | 4/1992 | Fowler | 606/213 |
| 5,108,430 | * | 4/1992 | Ravo | 623/12 |
| 5,116,357 | * | 5/1992 | Eberbach | 606/213 |
| 5,122,155 | | 6/1992 | Eberbach | 606/213 |
| 5,141,515 | | 8/1992 | Eberbach | 606/151 |
| 5,147,374 | | 9/1992 | Fernandez | 606/151 |
| 5,171,148 | | 12/1992 | Wasserman et al. | 433/215 |
| 5,219,077 | | 6/1993 | Transue . | |
| 5,246,455 | * | 9/1993 | Shikani | 623/10 |
| 5,249,682 | | 10/1993 | Transue | 206/438 |
| 5,254,133 | * | 10/1993 | Seid | 606/215 |
| 5,258,000 | * | 11/1993 | Gianturco | 606/151 |
| 5,292,328 | | 3/1994 | Hain et al. | 606/151 |
| 5,297,714 | | 3/1994 | Kramer | 227/175 |
| 5,316,543 | | 5/1994 | Eberbach | 600/37 |
| 5,334,217 | | 8/1994 | Das . | |
| 5,356,432 | | 10/1994 | Rutkow et al. | 623/11 |
| 5,366,460 | | 11/1994 | Eberbach | 606/151 |
| 5,366,478 | * | 11/1994 | Brinkerhoff et al. | 660/213 |
| 5,370,650 | | 12/1994 | Tovey et al. . | |
| 5,397,331 | | 3/1995 | Himpens et al. | 606/151 |
| 5,397,332 | | 3/1995 | Kammerer et al. | 606/151 |
| 5,423,777 | * | 6/1995 | Tajiri et al. | 604/294 |
| 5,456,720 | | 10/1995 | Schultz et al. . | |
| 5,569,273 | | 10/1996 | Titone et al. | 606/151 |
| 5,578,045 | | 11/1996 | Das | 606/151 |
| 5,686,090 | | 11/1997 | Schilder et al. | 424/423 |
| 5,690,674 | * | 11/1997 | Diaz | 606/213 |
| 5,861,003 | * | 1/1999 | Latson et al. | 606/213 |

* cited by examiner

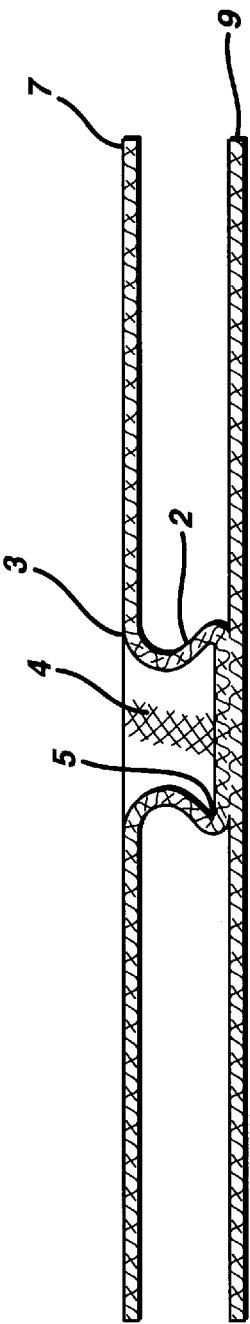
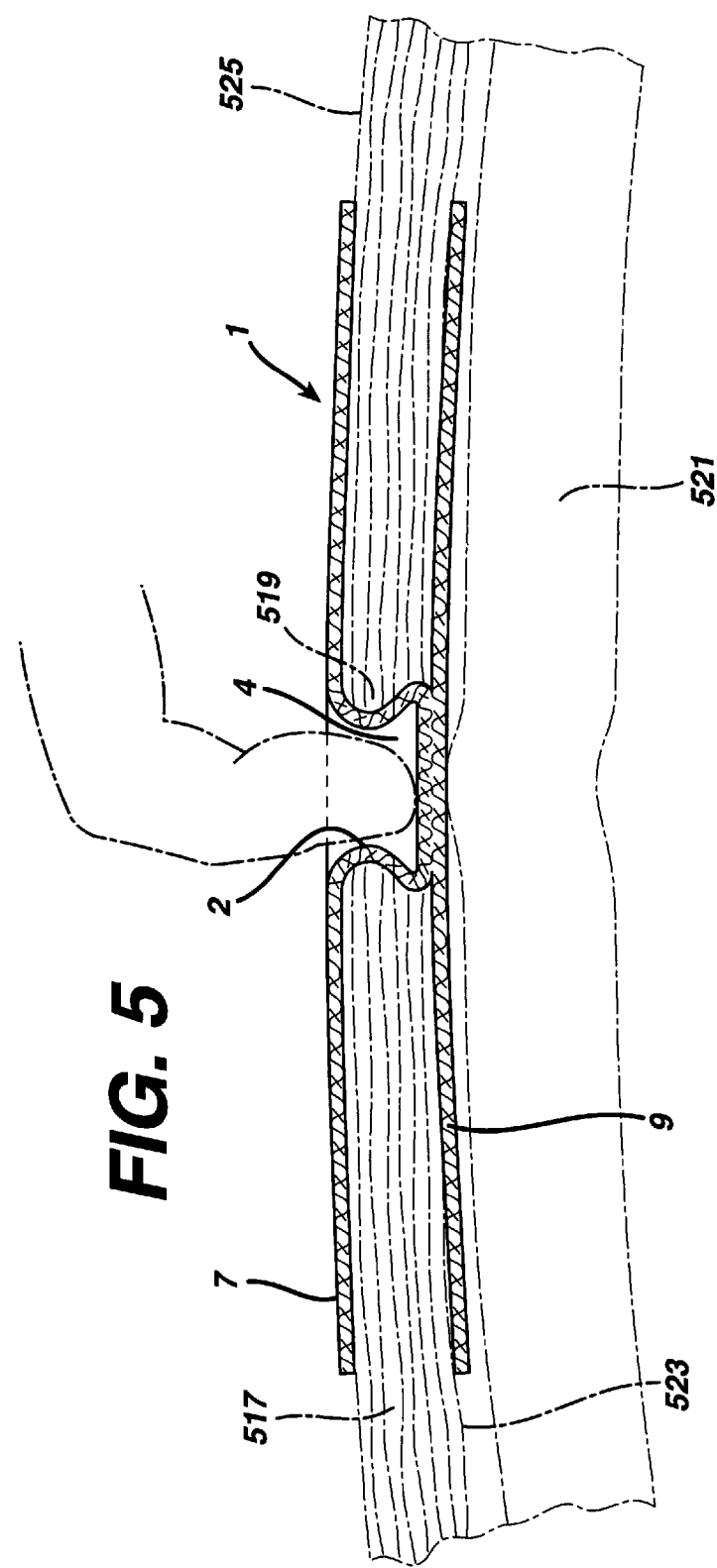
FIG. 4
FIG. 5

PROSTHETIC DEVICE FOR THE REPAIR OF A HERNIA

This patent application claims priority from provisional patent application Ser. No. 60/057,093, filed Aug. 27, 1997. The present invention relates to prosthetic devices and methods used to repair or obturate a hernia.

FIELD OF THE INVENTION

Background of the Invention

In conventional techniques, hernial canal repair is generally carried out by suturing. However, that method of repair is not entirely satisfactory: given that the suture line is subject to a large amount of tension, there is a risk of tearing, which could then lead to recurrence of the hernia.

In order to mitigate that disadvantage, tension-free hernia repair techniques have been proposed.

In particular, a known technique is to position a sheet of synthetic prosthesis material, of knit or woven mesh, over the hernial canal, to reinforce or replace the weakened tissue. For example, in open surgical repair of an inguinal hernia, a sheet or patch of mesh may be used which is positioned on the inguinal ring, on the side remote from the peritoneum, this sheet being slit to allow the spermatic cord to pass, and the two tails of the patch are then wound around the spermatic cord. The barrier thus created makes it possible for the inguinal canal floor to regenerate.

Such a barrier-forming sheet may also be positioned by non-invasive surgery. A device using a trocar to deploy prosthesis sheets inside the abdominal cavity, on the peritoneum, is described in EP 0 544 485, for example.

Another tension-free repair technique, which may be used in combination with the above-mentioned technique, consists in obturating the hernial canal with a prosthesis device.

Usually a surgeon makes a device by rolling a patch cut from prosthesis material in order to obtain a cylinder of appropriate dimensions (i.e., such described by I. L. Lichtenstein and J. M. Shore, Simplified Repair of Fermoral and Recurrent Inguinal Hernias by a "Device" Technic. Amer. Journal of Surgery 1979; 138: 788–793).

Other shapes of prosthesis device are also used, such as rectangular devices, conical devices or collared devices, enabling them to be positioned relative to the hernial canal. The following may be consulted in that respect: "Prostheses in Abdominal Wall Hernia", Robert Bendavid, RG Landes Company, Austin, pages 375–379, 380–382, 383–388, 389–398, 408–410, 411–412, 413–414, 446–449, and also U.S. Pat. Nos. 5,116,357 and 5,356,432.

Other known prostheses are constituted by cylindrical devices terminating at one end with prosthesis sheets for suturing by the surgeon to the non-weakened muscles on either side of the hernial canal to complement the obturation provided by the device. In that respect reference may advantageously be made to U.S. Pat. Nos. 5,141,515; 5,147,374; 5,219,077; and U.S. Pat. No. 5,249,682.

The object of the invention is to propose a prosthesis device which is simple in structure and simple to manipulate and which is also very effective.

SUMMARY OF THE INVENTION

The invention, therefore, provides a prosthetic device to repair a hernia defect which in one embodiment, comprising a canal insert having a proximal end and distal end; the proximal end being attached to a collar and the distal end being attached to and covered by a sheet.

In another embodiment of the present invention there is provided a prosthesis device to repair a hernia defect, the device comprising a canal insert for extending through said hernial canal, having a proximal end and a distal end; the proximal end being attached to a collar and the distal end of the canal insert being attached and covered by a pouch.

With such a structure, the canal insert, which is inserted in the hernia defect for obturation, is reinforced by a barrier-forming part which may either constitute a sheet or a pouch which provides very good resistance to intra-abdominal pressure because it is inserted on the inside of the hernial cavity and not on the outside.

Other characteristics and advantages of the invention can be seen from the following description. This description is intended as an illustration and is not limiting.

BRIEF DESCRIPTION OF THE FIGURE

FIG. 4 is a cross-sectional view illustrating a first possible embodiment of the invention (1).

FIG. 5 is a cross-sectional view illustrating the placement of the first possible embodiment of the invention (1) implanted in the abdominal wall (517).

DETAILED DESCRIPTION

Figure 1:
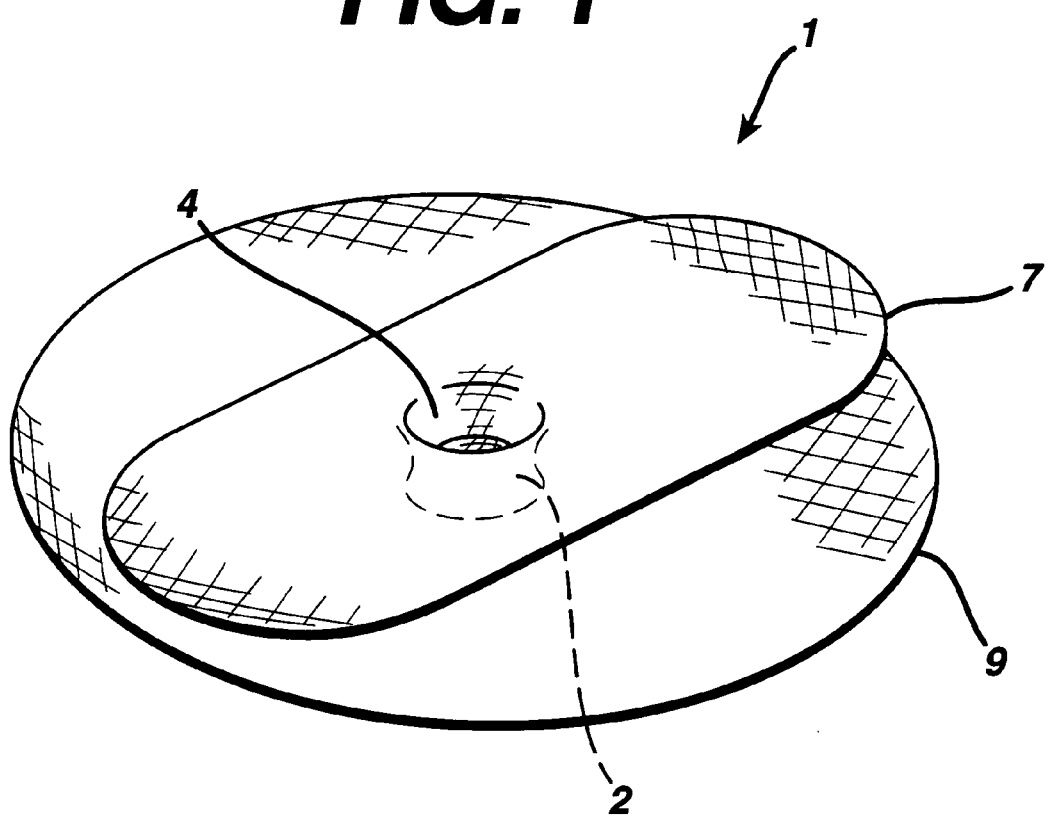
FIG. 1 is a prospective view of the first embodiment of the hernia prosthesis of the invention (1).
Figure 2:
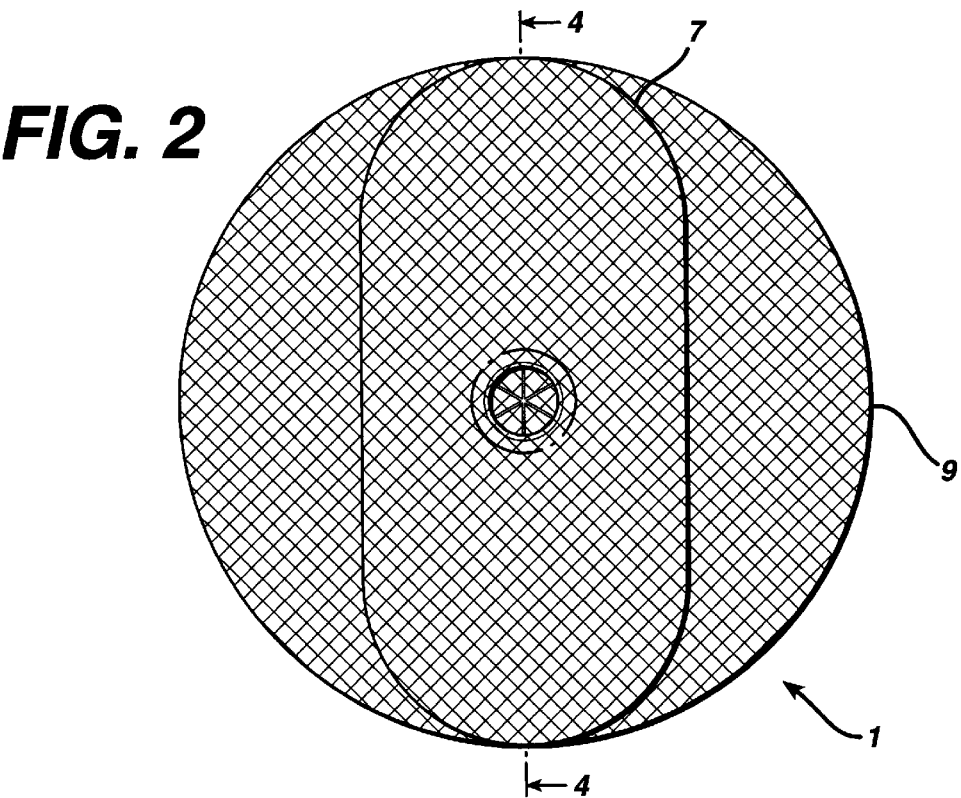
FIG. 2 is an illustration showing the top view of the first embodiment of the invention (1).

A perspective of one embodiment of the invention is shown in FIG. 1. The first embodiment of the invention 1 illustrated in FIG. 1 and shown in cross-section in FIG. 4 comprises three main parts: a cannular part or insert 2, which has a proximal end 3 and a distal end 5. The proximal end 3 is attached to the second part, a collar 7. The distal end 5 is attached to the third part, base 9, which is to be inserted inside the abdominal cavity to constitute a barrier at the internal canal of the hernial canal.

In a preferred embodiment, the canal insert 2 between the proximal end and the distal end 5 has a passage 4 having a geometric cross-section of sufficient size to allow the insertion of a finger or instrument (particularly preferred are passages that are cylindrical in shape). The passage 4 is shown in FIGS. 1, 4 and 5.

The canal insert 2 is attached to a collar 7 at its proximal end 3 to be positioned on the outside of the hernial cavity.

At this end, the collar 7 constitutes a base to facilitate fixation of the device which may be by suturing of the device by the surgeon. In a variant, the collar may also be constituted by a disk-shaped sheet fixed on the end of the canal insert 2.

Figure 3:
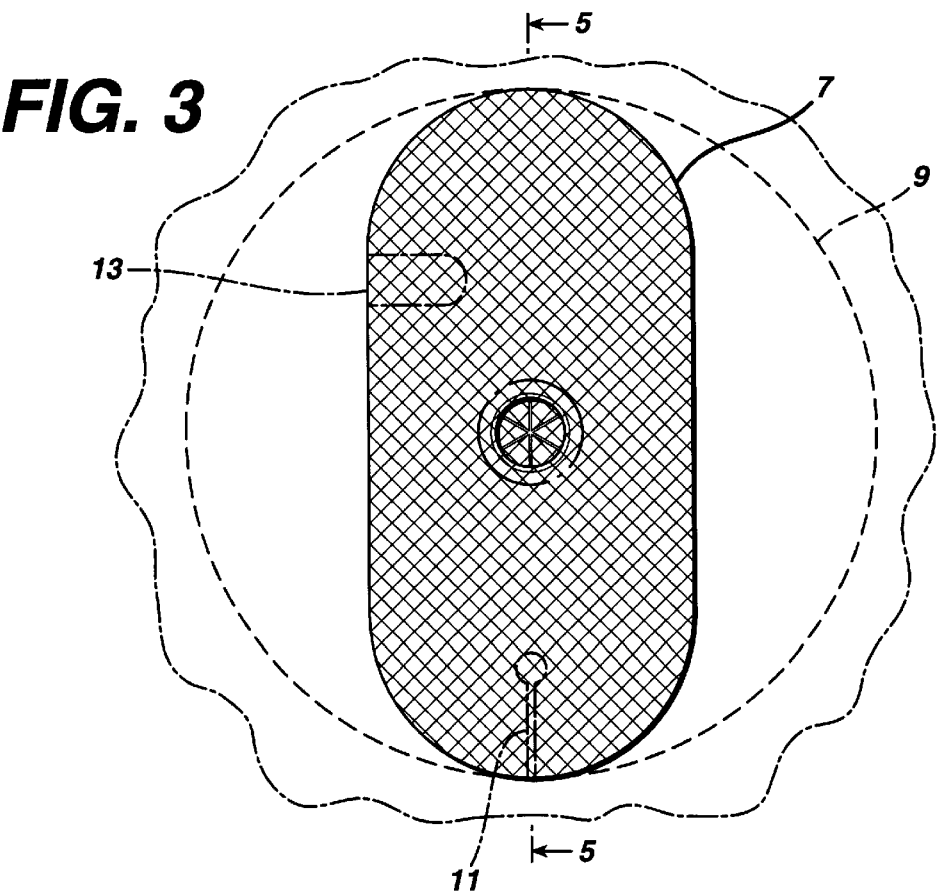
FIG. 3 is a perspective view showing the canal insert (2) place within a hernial canal with the base (9) shown in phantom implaced intra-abdominally.
Figure 6:
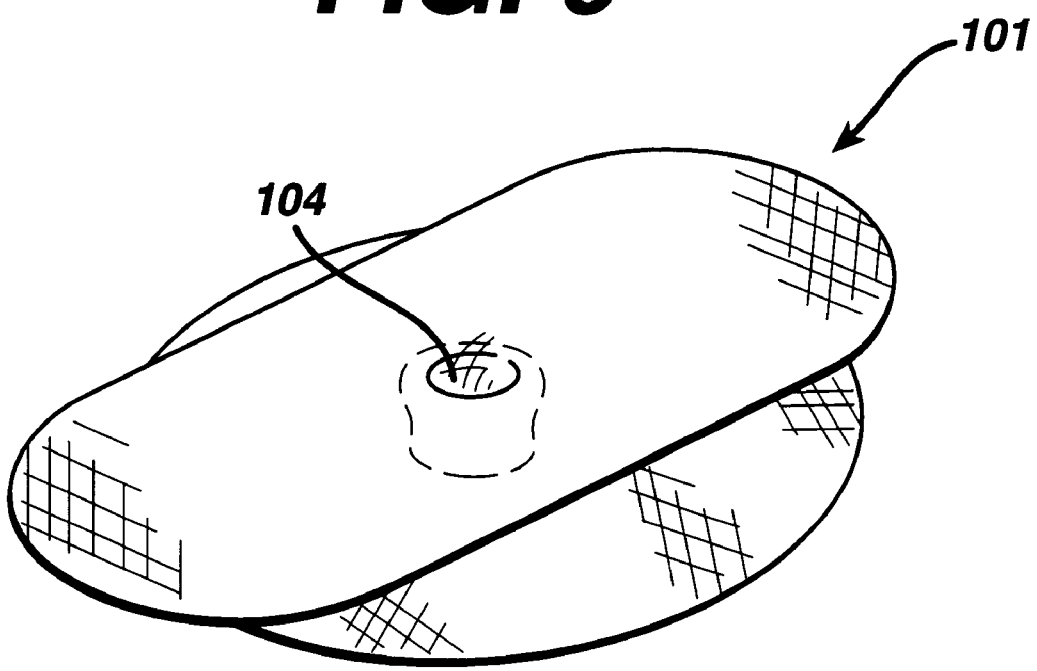
FIG. 6 is a prospective view of the second possible embodiment of the invention (101) having a canal (104).
Figure 7:
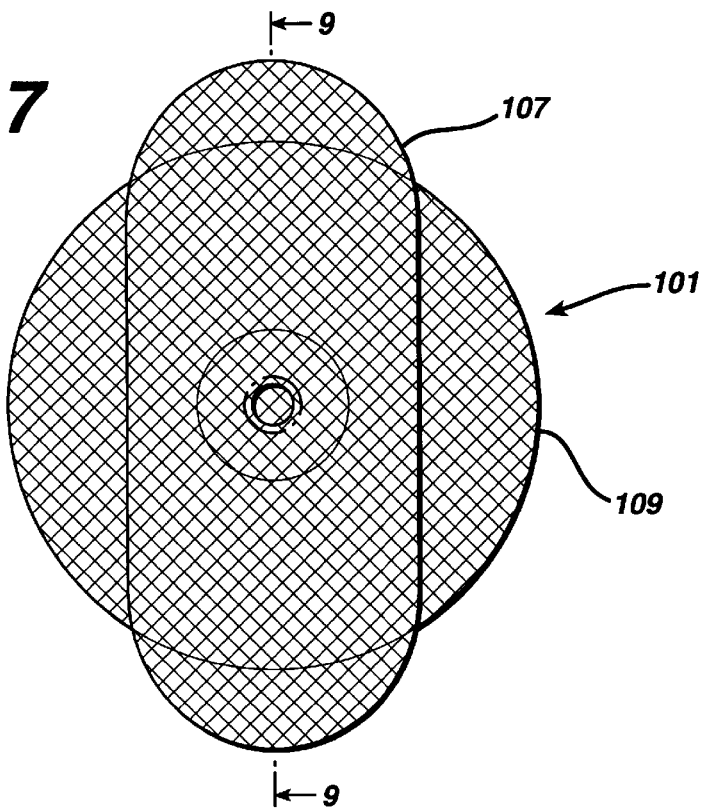
FIG. 7 is a top view of the second possible embodiment of invention (101).
Figure 8:
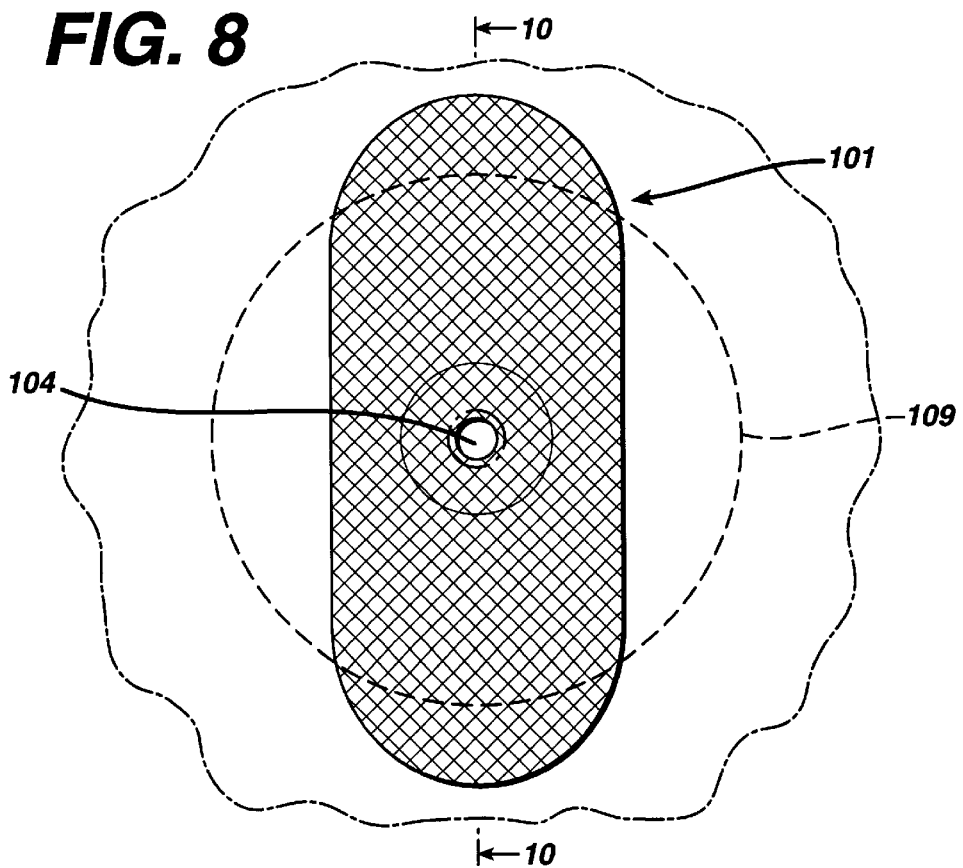
FIG. 8 is a perspective view of the second possible embodiment of the invention (101) illustrating the canal insert (102) placed within a hernial canal, with the sheet (109) shown in phantom implaced intraabdominally.
Figure 9:
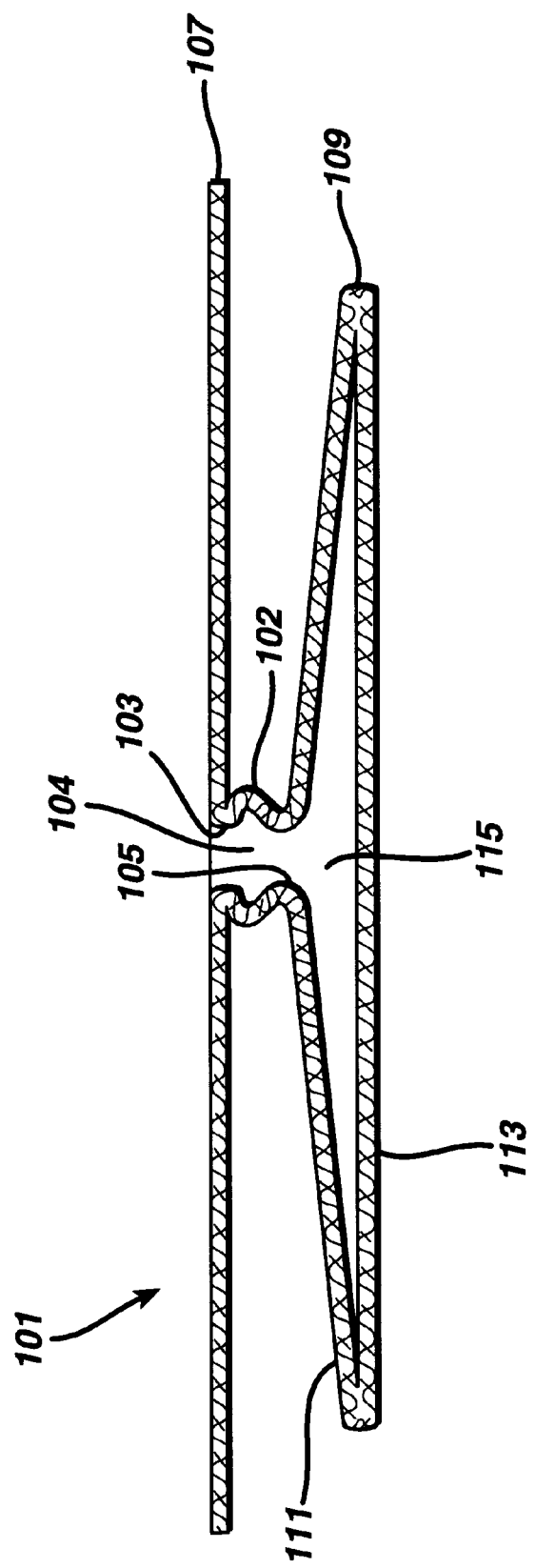
FIG. 9 is a cross-section view illustrating the second possible embodiment of the invention (101).

Of course the collar 7 and the base 9 may be of a shape other than circularly symmetrical. In particular the collar 7 may extend in one or more directions as one or more segments, thereby facilitating suturing in those directions. The collar 7 may also be notched (i.e. with a key-hole 11, semi-circular notch 13, or other notch shape) to facilitate the passage of the spermatic cord when the device is used in indirect hernia procedures as is illustrated in FIG. 3. The distal end 5 of canal insert 2 to be positioned on the inside of the cavity, is attached to and extended by the base 9 which may be a single sheet of material.

In an alternate embodiment of the present invention 101 the base 109 may be composed of a double sheet (as is illustrated in cross-section in FIGS. 6–10). The two layers 111 and 113, are folded over one another to form a substantially flat pouch 115, of circular or elliptical periphery, for example. The second embodiment of the invention as shown in cross-section in FIG. 9 comprises a canal insert 102 having a first end 103 and second ends 105. The first end 103 is attached to a collar 107 and the base 109 is attached to the proximal end of the canal insert 102. The base 109 comprises at least two sheets respectively 111 and 113. The sheets are attached and form a pouch 115. The passage 104 and is designed to allow a finger or surgical instrument to be inserted into the pouch 115.

The device-forming parts 1, 2 and the sheet(s) of part 3 are made of one or more biocompatible sheet materials. The material(s) from which these parts are made is/are selected so as to be inert and infection-resistant, and so as to be quickly incorporated into tissue. By way of example, the device-forming parts 1, 2 and the sheet(s) of part 3 may be made of the same or different synthetic or natural material. The material(s) from which these parts are made is selected so as to be inert and infection-resistant, and to be biocompatible with tissue. Numerous biocompatible absorbable and nonabsorbable materials can be used for parts 1, 2 and 3. Suitable nonabsorbable materials for use in parts 1, 2 and 3 include, but are not limited to, cotton, linen, silk, polyamides (polyhexamethylene adipamide (nylon 66), polyhexamethylene sebacamide (nylon 610), polycapramide (nylon 6), polydodecanamide (nylon 12) and polyhexamethylene isophthalamide (nylon 61) copolymers and blends thereof), polyesters (e.g. polyethylene terephthalate, polybutyl terphthalate, copolymers and blends thereof), fluoropolymers (e.g. polytetrafluoroethylene) and polyolefins (e.g. polypropylene including isotactic and syndiotactic polypropylene and blends thereof, as well as, blends composed predominately of isotactic or syndiotactic polypropylene blended with heterotactic polypropylene and polyethylene). Suitable absorbable materials for use in parts 1, 2 and 3 include, but are not limited to, homopolymers and copolymers of glycolide, lactide (which includes L-, D-, and mesoforms of lactide and mixtures thereof), ε-caprolactone, p-dioxanone, trimethylene carbonate, 1,4-dioxepan-2-one, poly(alkylene oxalate), and mixtures of such polymers with each other and with other compatible absorbable compositions as those described; for example, in U.S. Pat. No. 3,636,952 and U.S. Pat. No. 2,683,136.

The sheets that comprise parts 1, 2 and 3 may be constructed in a variety of way and may be films, felts, knits, wovens, crochets, braided materials or combinations thereof. Numerous surgical meshes, nets or films have been described in the literature and reference may be made to the following patents: U.S. Pat. No. 2,761,444; U.S. Pat. No. 3,054,406; U.S. Pat. No. 3,124,136; U.S. Pat. No. 4,347,847; U.S. Pat. No. 4,633,873; U.S. Pat. No. 4,769,038; U.S. Pat. No. 5,092,884; U.S. Pat. No. 5,292,328; U.S. Pat. No. 5,569,273; PCT/GB95/01786 and EP 0 698 395 A1, all of which are hereby incorporated by reference herein. Examples of suitable sheet materials include but are not limited to, polyester, polytetrafluoroethylene, expanded polytetrafluoroethylene or polypropylene mesh (such as Prolene™ Surgical Mesh from Johnson & Johnson), etc. The sheets will preferably be surgical mesh material. Surgical mesh materials are commonly knitted monofilaments, but may also be multifilaments. Additionally, the size of the filaments used to manufacture surgical meshes may vary depending on the structure and desired properties of the knitted material.

For example, the canal insert 2 may be approximately 1.27 cm high and 1.9 cm in diameter; if the collar 7 is oval the major axis may be approximately 10 cm and the minor axis 4.5 cm; if the base is circular, its diameter is for example 7.5 cm; knitted from 0.15 mm (6 mil) polypropylene monofilament.

In order to insert the prosthesis device in hernial canal 519, in the abdominal wall 517, the surgeon, having dissected the peritoneal sac 521 and pushing it back into the cavity, then bunches base 9 into a tubular shape and introduces the base 9 into the hernial cavity by pushing the base through the hernia canal 519 using a finger inserted into passage 4. The surgeon will then push the base 9 into the peritoneal cavity. The surgeon's finger will temporarily push the canal insert 2 into the interior of the peritoneal cavity to create additional space to allow the base 9 to fully deploy against the inside wall of the abdomen 523. As illustrated in FIG. when finally positioned in the patient canal insert 2 is positioned in such a way that it extends through hernial canal 519, the base 9 being brought to bear on the inside of the abdominal wall and the collar 7 will be positioned on the outside of the abdominal wall 525. The second embodiment of the invention is inserted in a different manner.

Figure 10:
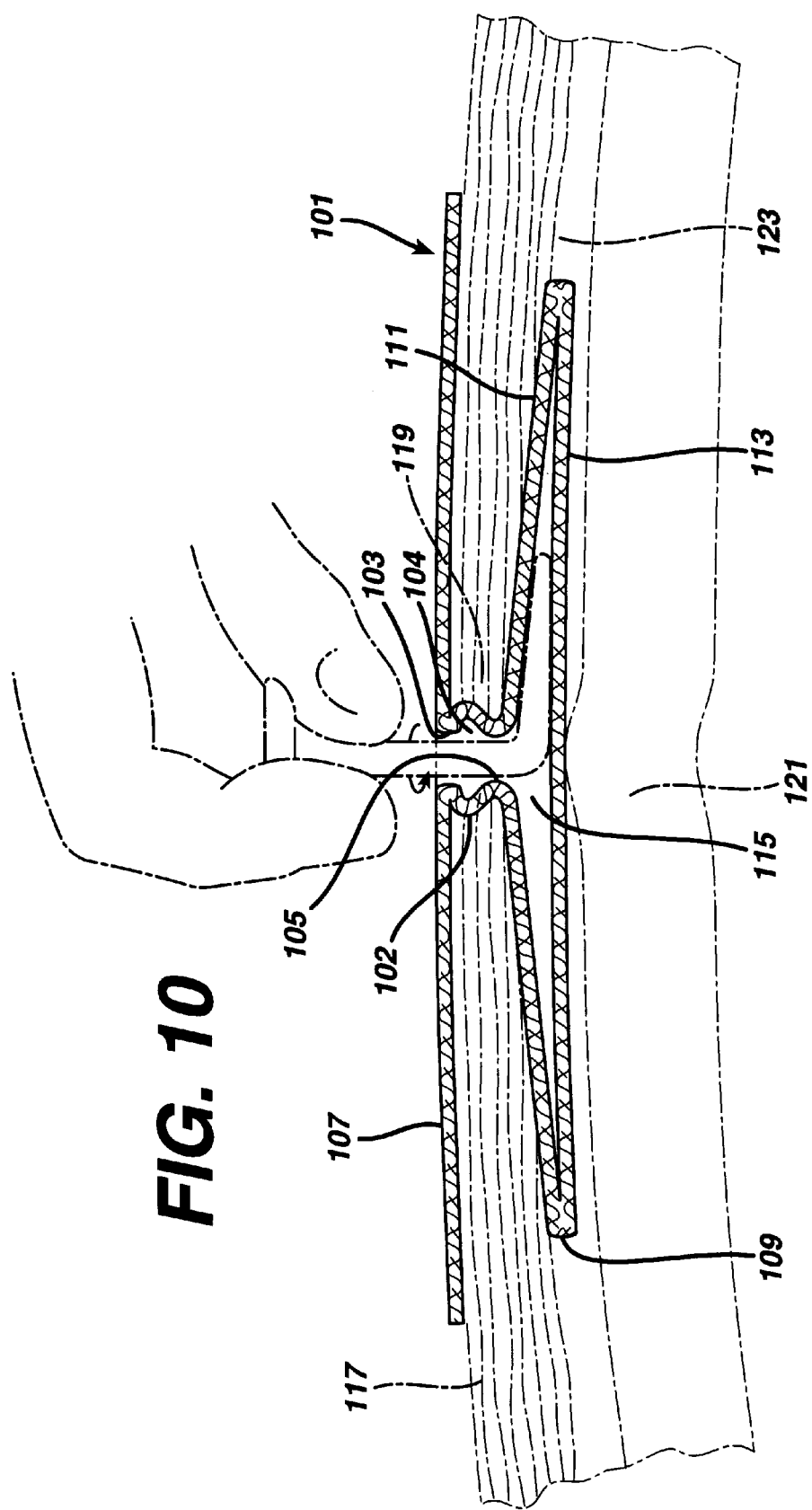
FIG. 10 is a cross-sectional view illustrating the placement of the second possible embodiment of the invention in the abdominal wall (117).
Figure 11:
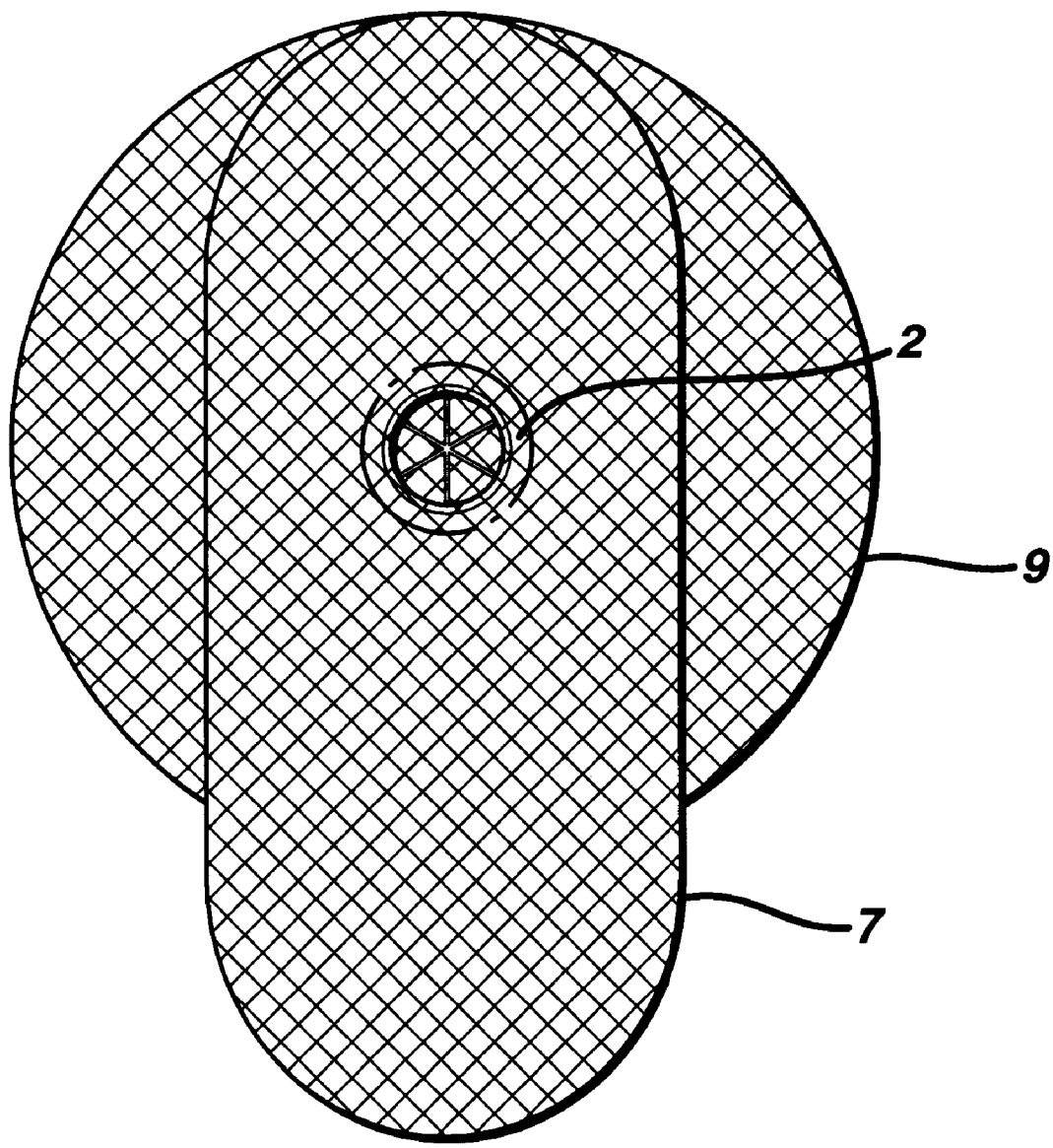
FIG. 11 is a perspective view of yet another embodiment of the present invention in which the collar (7) and/or canal insert (2) is not centered on the base (9).

The second embodiment of the invention 101 shown in FIG. 10 is inserted into the hernial canal 119, the surgeon, having dissected the peritoneal sac 121 and pushing it back into the cavity, then introduces the base 109 into the outside of the abdominal cavity, while inserting the canal insert in such a way that it extends through the hernial canal 119, the collar 107 being brought to bear on the outside of the abdominal wall 117. The surgeon then introduces the end of a surgical instrument (i.e. a cannula) or his finger into the pouch 115 through the passage 104 and deploys the patch so that the two sheets 111 and 113 are properly superposed and inserted, under the effect of intra-abdominal pressure, against the inside face of the abdominal cavity 123.

Once the pouch 115 is correctly deployed against the inside face of the wall of the abdominal cavity 123, the surgeon may sutures the collar 107 to the abdominal wall 117.

As can be easily understood, the above-described prosthesis devices have a number of advantages.

They are very simple to make and to insert.

In addition, it is very effective. In particular the barrier-forming part 3, because it is positioned inside the hernial cavity and not externally, provides excellent resistance to intra-abdominal pressure.

Advantageously, the surgeon may also introduce fiber or foam material through the passage 104, to fill the pouch 115 and the passage 104 so as to constitute a ball of fiber or foam in the pouch to absorb abdominal pressure elastically while spreading the force exerted at the hernial canal over a portion of the wall of the hernial cavity surrounding said canal.

The prosthetic device of the present invention may be manufactured by any appropriate technique known in the art. For Example the mesh may be cut into the appropriate shape by a cutting blade, hot knife, or ultrasonic cutting device (the last two cutting devices may provide more uniform edges). The three dimensional structure of the device can be formed by shaping a sheet of mesh over a heated tool and cooling the sheet material to set the shape. In the case of polypropylene knitted mesh, the mesh may be thermoformed over a heated tool in the range of from about 175° F. to about 320° F. and preferably about 245° F. under suitable pressure for a suitable amount of time (at least 10 seconds and preferably less than 30 minutes). The thermoforming should be conducted in a manner that does not distort or weaken the mesh structure. Generally polypropylene mesh should be compressed between a male and female forming tool which are closed together at a speed in the range of from about 2 to about 25 cm per minute and preferable at a speed of in the range of from about 5 to about 7.5 cm per minute. Polypropylene meshes should generally be heated for in the range of from about 2 to about 5 minutes and cooled to below room temperature to set the shape. Currently it is preferred to cool polypropylene mesh to 55° F. or less for in the range of from about 2 to about 5 minutes. The shaped sheet may then be attached to the base by an appropriate attachment means (i.e. sewing, gluing or welding). One appropriate method for attaching two sheets polypropylene mesh is to ultrasonically weld the two pieces together. It is advisable with some materials (i.e. polypropylene mesh) to support the three dimensional shape in its package to insure the device maintains its shape.

We claim:

1. A mesh prosthesis device to repair a hernia, the device consisting essentially of a canal insert having a proximal end and distal end; the proximal end being attached to a collar and the distal end being attached to and covered by a base wherein a passage extends from the collar to the base to facilitate the placement of the device and wherein the canal insert, the collar, and the base comprise a non-absorbable or absorbable sheet material selected so as to be incorporated into tissue.

2. A device according to claim 1, wherein the base is a sheet.

3. A device according to claim 1, wherein the base is a sheet composed of two layers.

4. A device according to claim 3, wherein the two layers form a pouch.

5. A device according to claim 4, wherein a path way is formed through the canal insert into the pouch.

6. A device according to claim 4, wherein the pouch is filled with a fiber or foam-type prosthetic material.

7. A device according to claim 1 wherein the collar is notched.

8. The device of claim 2 wherein the base is a sheet with a single layer and attached to and terminating the canal insert.

* * * * *